US00PP21924P2

(12) United States Plant Patent
Nielsen

(10) Patent No.: US PP21,924 P2
(45) Date of Patent: May 17, 2011

(54) *GENTIANA* PLANT NAMED 'GENTO'

(50) Latin Name: *Gentiana scabra*
Varietal Denomination: Gento

(75) Inventor: Rune Harboe Nielsen, Odense N (DK)

(73) Assignee: Dalina APS, Odense N (DK)

( * ) Notice: Subject to any disclaimer, the term of this patent is extended or adjusted under 35 U.S.C. 154(b) by 0 days.

(21) Appl. No.: 12/657,064

(22) Filed: Jan. 13, 2010

(51) Int. Cl.
*A01H 5/00* (2006.01)

(52) U.S. Cl. ..... Plt./433

(58) Field of Classification Search ..... Plt./433
See application file for complete search history.

(56) References Cited

OTHER PUBLICATIONS

Print-out of application number and filing date from Community Plant Variety Office (CPVO) website for corresponding, CPVO application No. 2009/1279 filed Jul. 6, 2009 (5 pages). (http://www.cpvoextranet.cpvo.europa.eu).

*Primary Examiner* — Annette H Para
(74) *Attorney, Agent, or Firm* — Foley & Lardner LLP

(57) ABSTRACT

A new distinct cultivar of *Gentiana scabra* plant named 'GENTO', characterized by (1) upright to outward, compact and uniform plant habit; (2) moderate vigor; (3) globular plant shape, measuring about 11 cm in height and 20 cm in diameter; (4) uniform and freely branching with both basal and lateral branching; (5) yellow-green, RHS 146B, stems, measuring about 8 cm in length and 2 mm in diameter, and strong in strength that can support flowers without drooping; (6) about 35-45 flowers per plant, each flower measuring about 45 mm in depth and about 35 mm to 4- mm in diameter, and with a mature, upper petal surface color of violet-blue, RHS 96B, with small stains of yellow-green, RHS 144A; and (7) earlier production time to produce flowering plant.

5 Drawing Sheets

Latin name of the genus and species of the claimed plant: *Gentiana scabra.*

Variety denomination: 'GENTO'.

BACKGROUND OF THE INVENTION

The present invention relates to a new and distinct cultivar of *Gentiana* plant, botanically known as *Gentiana scabra* of the Gentianaceae family, commonly known as Japanese gentian, and hereinafter referred to by the cultivar name 'GENTO'.

The new *Gentiana scabra* cultivar is a product of a planned breeding program conducted by the inventor, Rune NIELSEN, in Odense N, Denmark. The objective of the breeding program is to develop a new *Gentiana scabra* variety with a good "gentian blue" flower, combined with a good growing character, with many shoots and branches.

The new *Gentiana scabra* 'GENTO' originated from a naturally-occurring mutation. Unprotected *Gentiana scabra* plant material was brought to Denmark in 1994 from Japan, and this unprotected *Gentiana scabra* plant material has been grown in a controlled breeding program in Naeldebakken, Denmark since 1994. From this unprotected *Gentiana scabra* plant material, a naturally-occurring mutation line designated by the inventor as 09.C001 resulted in 2007, after being propagated via tissue culture.

The new *Gentiana scabra* 'GENTO' was then further discovered and selected by the inventor, Rune Nielsen, as a single flowering plant within the progeny of the stated mutation line designated as 09.C001 in July 2007 in a controlled environment in Odense, Denmark.

Asexual reproduction of the new *Gentiana scabra* 'GENTO' by cuttings was first performed from January of 2008 in Odense, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'GENTO', which in combination distinguish this *Gentiana scabra* as a new and distinct cultivar:

1. Upright to outward, compact and uniform plant habit;
2. Moderate vigor;
3. Globular plant shape, measuring about 11 cm in height and 20 cm in diameter;
4. Uniform and freely branching with both basal and lateral branching;
5. Yellow-green, RHS 146B, stems, measuring about 8 cm in length and 2 mm in diameter, and strong in strength that can support flowers without drooping;
6. About 35-45 flowers per plant, each flower measuring about 45 mm in depth and about 35 mm to 4- mm in diameter, and with a mature, upper petal surface color of violet-blue, RHS 96B, with small stains of yellow-green, RHS 144A; and
7. Earlier production time to produce flowering plant.

Plants of the new *Gentiana scabra* 'GENTO' differ primarily from the plants of the parental *Gentiana scabra* line designated 09.C001 in production time. Plants of 'GENTO' produce flowers about 2 weeks earlier than plants of 09.C001.

No commercial cultivars most similar to the new *Gentiana scabra* 'GENTO' are known to the inventor in order to provide a comparison description.

BRIEF DESCRIPTION OF THE PHOTOGRAPHS

The accompanying photographs illustrate the overall appearance of the new *Gentiana* 'GENTO' showing the colors as true as is reasonably possible with colored reproductions of this type. Colors in the photographs may differ slightly from the color value cited in the detailed botanical description which accurately describe the color of 'GENTO'.

DETAILED BOTANICAL DESCRIPTION

Figure 1:
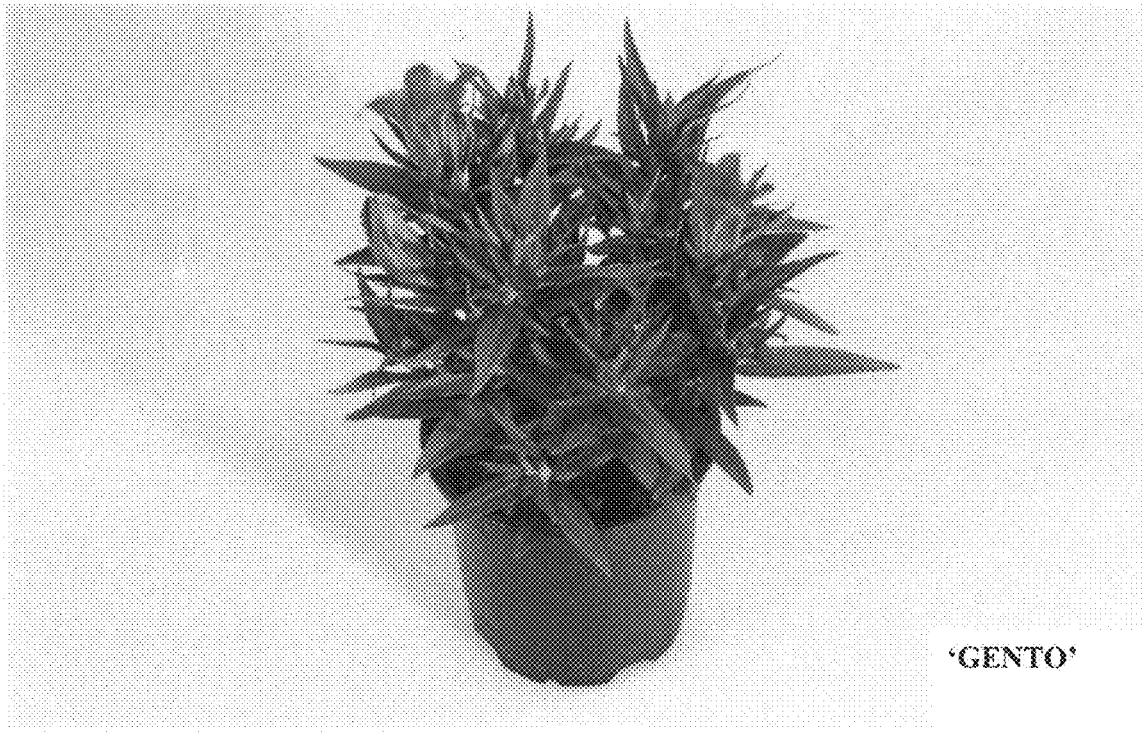
FIG. 1 shows a side view perspective of a typical flowering plant of 'GENTO' in a 11 cm pot, at 13 weeks of age after planting.
Figure 2:
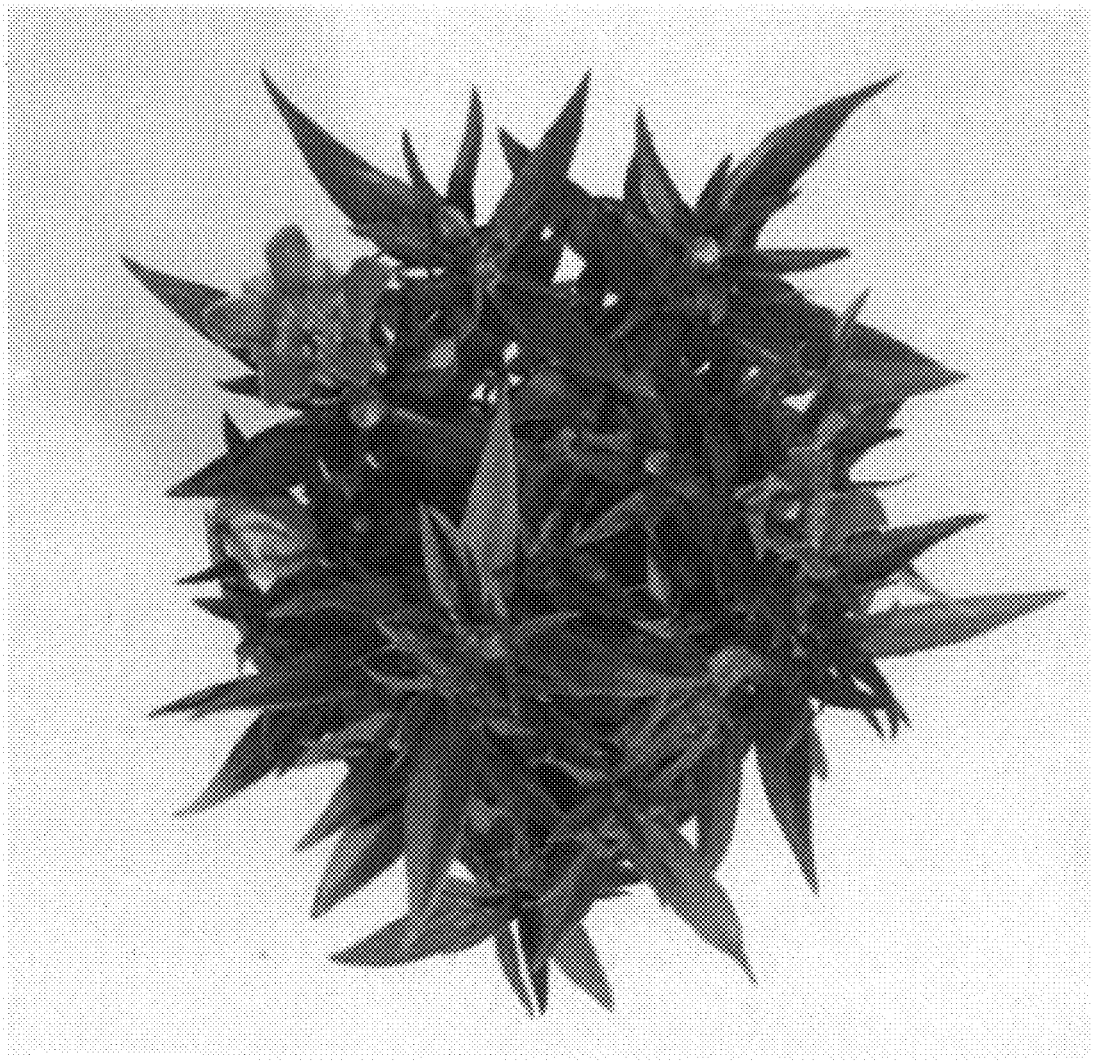
FIG. 2 shows a top view perspective of a typical flowering plant of 'GENTO' in a 11 cm pot, at 13 weeks of age after planting.
Figure 3:
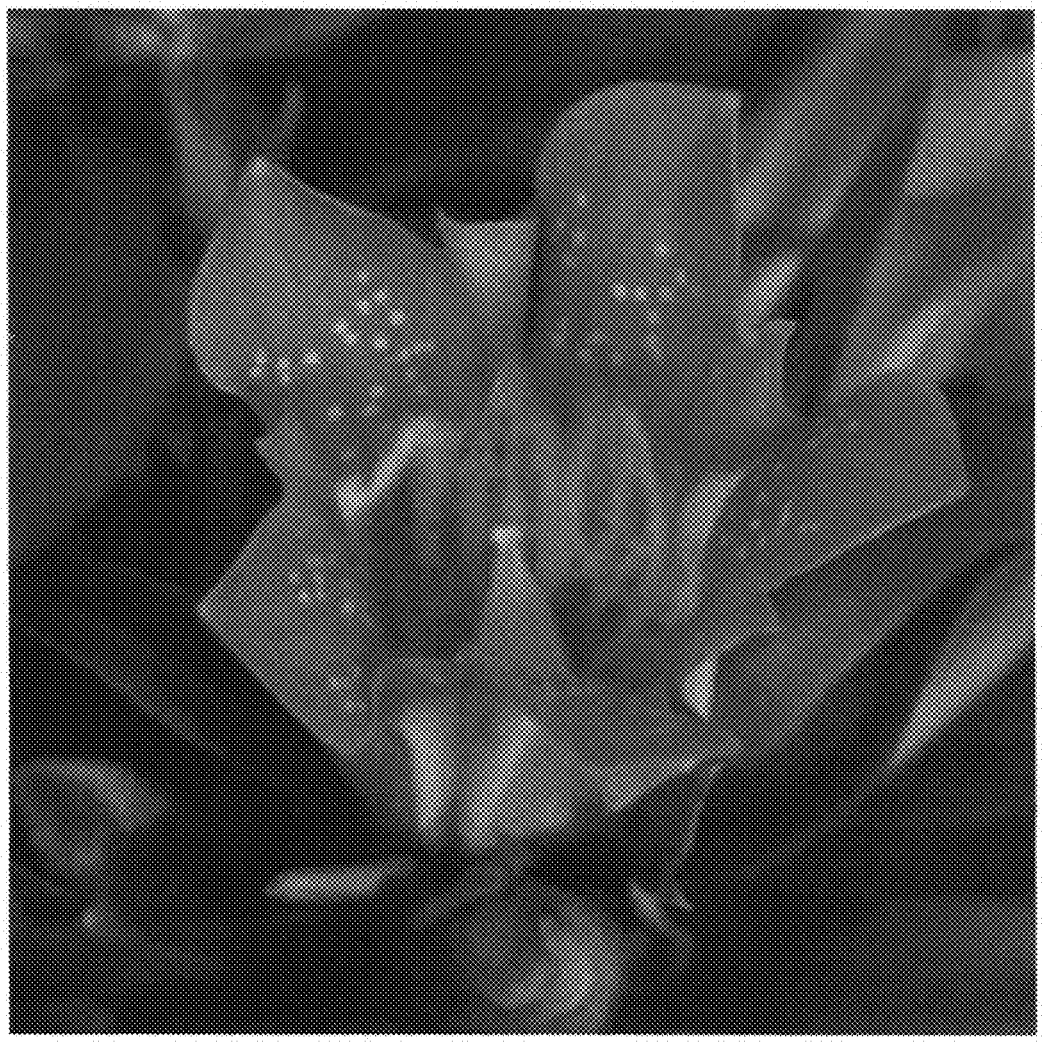
FIG. 3 shows a close-up view of the typical flower of 'GENTO' at 13 weeks of age after planting.
Figure 4:
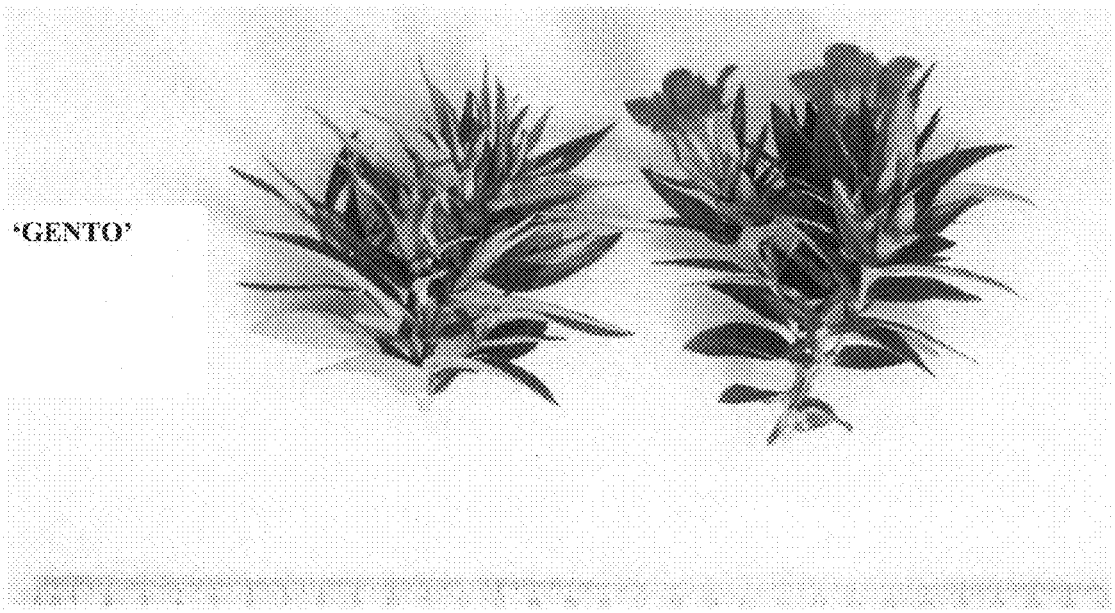
FIG. 4 shows a close-up view of the typical flower, buds and leaves of 'GENTO' at 13 weeks of age after planting.
Figure 5:
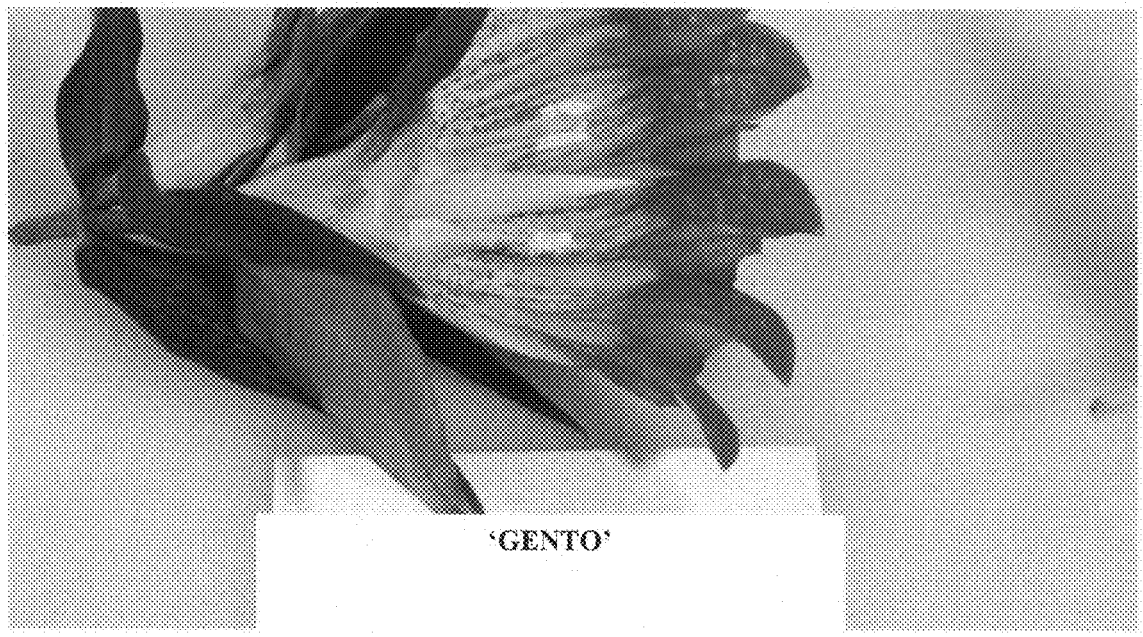
FIG. 5 shows a close-up view from the inside of the typical flower of 'GENTO' at 13 weeks of age after planting.

The new *Gentiana* 'GENTO' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Gentiana* 'GENTO' as grown in a glasshouse, equipped with heat, assimilation light and ebb/flood watering system in Odense, Denmark, under conditions which closely approximate those generally used in commercial practice. The plants described were grown in an average day temperature of 22° C. and an average night temperature of 20° C., giving an average overall temperature of 21° C. Plants were grown in long day conditions (greater than 14 hours). The first 5 weeks after potting, the plants were given assimilation light to meet a total of 50 klux per day. From the $6^{th}$ week until flowering, the plants were given a total of >120 klux per day. Nutrition was added to the water, and adjusted to keep the EC level in the soil to about 2.0. Plant growth was regulated with BONZI 1% applied as light sprays.

The color descriptions refer to The Royal Horticultural Society (R.H.S.) Colour Chart 2001 edition. Color values were taken under October daylight conditions around noon in Odense, Denmark.

The age of the 'GENTO' plants described is 16 weeks from potting.

Classification:

*Botanical.*—*Gentiana scabra.*

Propagation:

*Type.*—Stock plants from tissue culture. Production from top cuttings.

*Time and temperature to initiate roots.*—Winter-spring: About 14 to 16 days at 20° C. to22° C. in tunnels in a greenhouse.

*Time and temperature to produce a rooted young plant.*—Winter-spring: About 35 to 40 days at 18° C. to 20° C. in a greenhouse.

*Rooting habit.*—Fine, fibrous and branching.

Plant description:

*General appearance and form.*—Perennial, herbaceous plant with upright to outward, compact and uniform plant habit. Campanulate, tubular flowers arranged in terminal and axillary clusters.

*Growth rate.*—Moderate vigorous. Growing about 5 cm per month until buds are visible.

*Plant height.*—About 10 cm to 12 cm.

*Plant width* (*spread*).—About 18 cm to 22 cm.

*Crop time to produce a mature flowering plant.*—Propagation period is 5 weeks. After potting, about 13 weeks are required to produce finished flowering plants in 10 cm pots.

Stem:

*Shape.*—Round.

*Length.*—About 6 cm to 10 cm.

*Diameter.*—About 1.8 mm to 2.0 mm.

*Strength.*—Strong.

*Aspect.*—Upright to outward.

*Texture.*—Hoary, with 6 visible veins along stem, giving the stem a 6-angle look.

*Color.*—Immature: Yellow-green, RHS 145A. Mature: Yellow-green, RHS 146B. Old: Yellow-green, RHS 146B with stains of Greyed-purple, RHS 187B near node.

Branches:

*Branching habit.*—Basal branching with lateral branching.

*Number of branches per plant.*—About 8 to 14.

*Length* (*including flowers*).—About 5 cm to 12 cm.

*Diameter.*—About 1 mm to 2 mm.

*Strength.*—Strong.

*Aspect.*—Initially upright then bending outwardly.

*Texture.*—Hoary, with 6 visible veins along stem, giving the stem a 6-angle look.

*Color.*—Immature: Yellow-green, RHS 145A. Mature: Yellow-green, RHS 146B.

*Internode length.*—About 1.8 cm to 2.2 cm.

*Internode color.*—Immature: Yellow-green, RHS 145A. Mature: Yellow-green, RHS 146B.

Foliage description:

*Arrangement.*—Opposite, simple, sessile.

*Number of leaves per stem/branch.*—About 3-5 pairs per stem/branch.

*Length.*—About 30 mm to 48 mm.

*Width.*—About 13 mm to 15 mm.

*Overall shape of leaf.*—Lanceolate to elliptic.

*Shape at apex.*—Acute.

*Shape at base.*—Cuneate.

*Margin.*—Entire.

*Texture.*—Upper surface: Very fine tessellate pattern. Lower surface: Very fine tessellate pattern.

*Color of developing foliage.*—Upper surface: Green, RHS 137A. Lower surface: Yellow-green, RHS 146B.

*Color of mature foliage.*—Upper surface: Green, RHS 135A. Lower surface: Yellow-green, RHS 146B.

*Venation pattern.*—Parallel.

*Venation color.*—Upper surface: Green, RHS 135A. Lower surface: Yellow-green, RHS 146B.

Flower description:

*Appearance.*—Terminal and axillary campanulate flowers, arising singularly or in small clusters, held above and beyond the foliage, facing upright or slightly outward.

*Natural flowering season.*—Grown outside in Denmark (temperate zone); 'GENTO' will flower in late August or early September.

*Time to flower.*—90 days when grown in glasshouse environment with heat and assimilation light in Denmark.

*Postproduction longevity.*—Flowers maintain good color and substance for 14 to 21 days on the plant, when grown in an outdoor environment in Denmark. (Longevity of individual flowers is dependent on temperature and light conditions) Inflorescences are not persistent.

*Quantity of inflorescences.*—Freely flowering; about 40 buds and open inflorescences per plant.

*Fragrance.*—None.

*Bud.*—Rate of opening (from showing c 2 to 5 days. Length: About 30 mm. Diameter: About 8 mm to 12 mm. Shape: Narrow elliptic. Texture: Glabrous. Color: Yellow-green, RHS 145D, at the base changing to greyed-purple, RHS N187B, on the middle and changing to yellow-green, RHS 146A, at the tip.

*Peduncle.*—Terminal flowers: None. Axillary flowers: Some have a short peduncle. Length: Up to 3 mm. Diameter: About 1.5 mm. Angle: About 30° from vertical. Strength: Strong. Texture: Glabrous. Color: Yellow-green, RHS 146C.

*Flower.*—Flower depth (height): About 45 mm. Flower diameter About 35 mm to 40 mm.

*Petals.*—Quantity per flower: 5. Arrangement: Single, bell-shaped, basally fused, tubular flowers. Length: About 40 mm to 45 mm. Width: About 12-16. Overall shape: Oblong and tubular. Shape at apex: Acute. Shape at base: Fused. Margin: Entire. Texture: Upper surface: Glabrous. Lower surface: Glabrous, Striate. Orientation: Initially 20° from vertical, close to 0° from vertical at middle of petal, with development to 180° from vertical at the tip of petal. Color (when opening): Outer surface: Green part of petal: Yellow-green, RHS 147B. Blue part of petal: Violet-blue, RHS 96B to RHS 97B. Inner surface: Upper 30% of petal: Violet-blue, RHS 95B with small stains of yellow-green, RHS 144A. Lower 70% of petal: White, RHS 155C with small stains of greyed-green, RHS 189A (some darker). Color (when fully opened): Outer surface: Green part of petal: Yellow-green, RHS 146B. Blue part: Violet-blue, RHS 96B to RHS 97B. Inner surface: Upper 30% of petal: Violet-blue, RHS 96B with small stains of Yellow-green, RHS 144A. Lower 70% of petal: White, RHS 155C with small stains of greyed-green, RHS 189A (some darker).

*Calyx.*—Form: Campanulate. Length: About 10-12 mm. Diameter: About 7-9 mm.

*Sepals.*—Number: 5. Length: About 25 mm. Width: About 5 mm to 6 mm. Overall shape: Lanceolate. Shape at apex: Acute. Shape at base: Fused. Margin: Entire. Texture: Upper surface: Tessellate (very fine). Lower surface: Tessellate (very fine). Color (mature): Upper surface: Green, RHS 141A. Lower surface: Green, RHS 144A. Color (when fully opened): Upper surface: Green, RHS 139A. Lower surface: Yellow-green, RHS 144A.

Reproductive organs:

*Androecium.*—Stamen number: 5. Stamen length: About 20 mm. Anther shape: Oblong, basifixed. Anther length: About 4.5 mm. Anther color: Yellow, RHS 11C. Filament length: About 15.5 mm. Filament color: Close to white, RHS 155D, at base to greyed-white, RHS 156A, near anther. Pollen amount: Abundant. Pollen color: Yellow, RHS 8B.

*Gynoecium.*—Quantity: 1. Pistil length: About 36 mm. Stigma shape: Bifid, curving round when receptive to pollen. Stigma size (receptive surface): Length: About 3.5 mm. Width: 1.5 mm. Stigma color (Receptive surface): White, RHS 155C. Ovary length: 20 mm. Ovary diameter: 3.5 mm. (When receptive to pollen). Ovary color: Yellow-green, RHS 145A.

Seed/fruit: Seed and fruit production has not been observed.

Disease/pest resistance: None observed.

Disease/pest susceptibility: Susceptibility to pathogens and pests common to *Gentiana* has not been observed.

Temperature tolerance: Hardy to USDA Hardiness Zone 7, if well established in the ground prior to the winter.

What is claimed is:

1. A new and distinct cultivar of *Gentiana scabra* plant named 'GENTO', as illustrated and described herein.

* * * * *

'GENTO'